United States Patent [19]

Kopfer

[11] 4,185,628
[45] Jan. 29, 1980

[54] COMPARTMENTAL SYRINGE

[76] Inventor: Rudolph J. Kopfer, 10 Ridgecrest Rd., Kentfield, Calif. 94904

[21] Appl. No.: 911,203

[22] Filed: May 31, 1978

[51] Int. Cl.² ............................................. A61M 5/00
[52] U.S. Cl. ............................ 128/218 M; 128/272.1; 222/145; 222/386
[58] Field of Search ............... 222/129, 130, 145, 386, 222/387; 128/218 M, 220, 218 P, 272, 237, 272.1; 206/219–221; 215/DIG. 8

[56] References Cited

U.S. PATENT DOCUMENTS

| | | | |
|---|---|---|---|
| 1,234,582 | 7/1917 | Trueblood | 128/218 R |
| 3,464,412 | 9/1969 | Schwartz | 128/218 M |
| 3,872,864 | 3/1975 | Allen | 128/218 M |
| 3,951,146 | 4/1976 | Chiquiar-Arias | 128/218 P |

Primary Examiner—H. Grant Skaggs
Attorney, Agent, or Firm—George B. White

[57] ABSTRACT

The syringe has an outer casing open at one end and a cylinder reciprocable within the casing in which latter works a plunger; the cylinder is spaced from the inner periphery of the casing to form an outer chamber and the space within the cylinder forms an inner chamber, each chamber to contain the ingredients to be mixed to form a composition for injection; means being provided at the discharge end of the casing for the attachment of a needle for injection; sealing means at the open end of the casing are extended outwardly along the cylinder to protect the exterior of the cylinder from contamination during its withdrawal for the purpose of mixing. In another form the discharge end of the cylinder is adapted to be extended through the discharge sealing gland to receive the syringe needle; the sealing gland at the discharge end of the cylinder has suitable spiral grooves facing the cylinder so that when the cylinder is retracted its nozzle end discharges into the spiral grooves; the inner and outer chambers are of such capacity that when the cylinder is in mixing position and when the cylinder is retracted to locate the nozzle, it enlarges the capacity of the outer chamber creating suction to facilitate the discharge of the contents of the inner chamber by the plunger without producing undue pressure in the outer chamber, a negative or vacuum effect is created within the combined inner and outer chamber environment when the cylinder is in mixing position.

18 Claims, 13 Drawing Figures

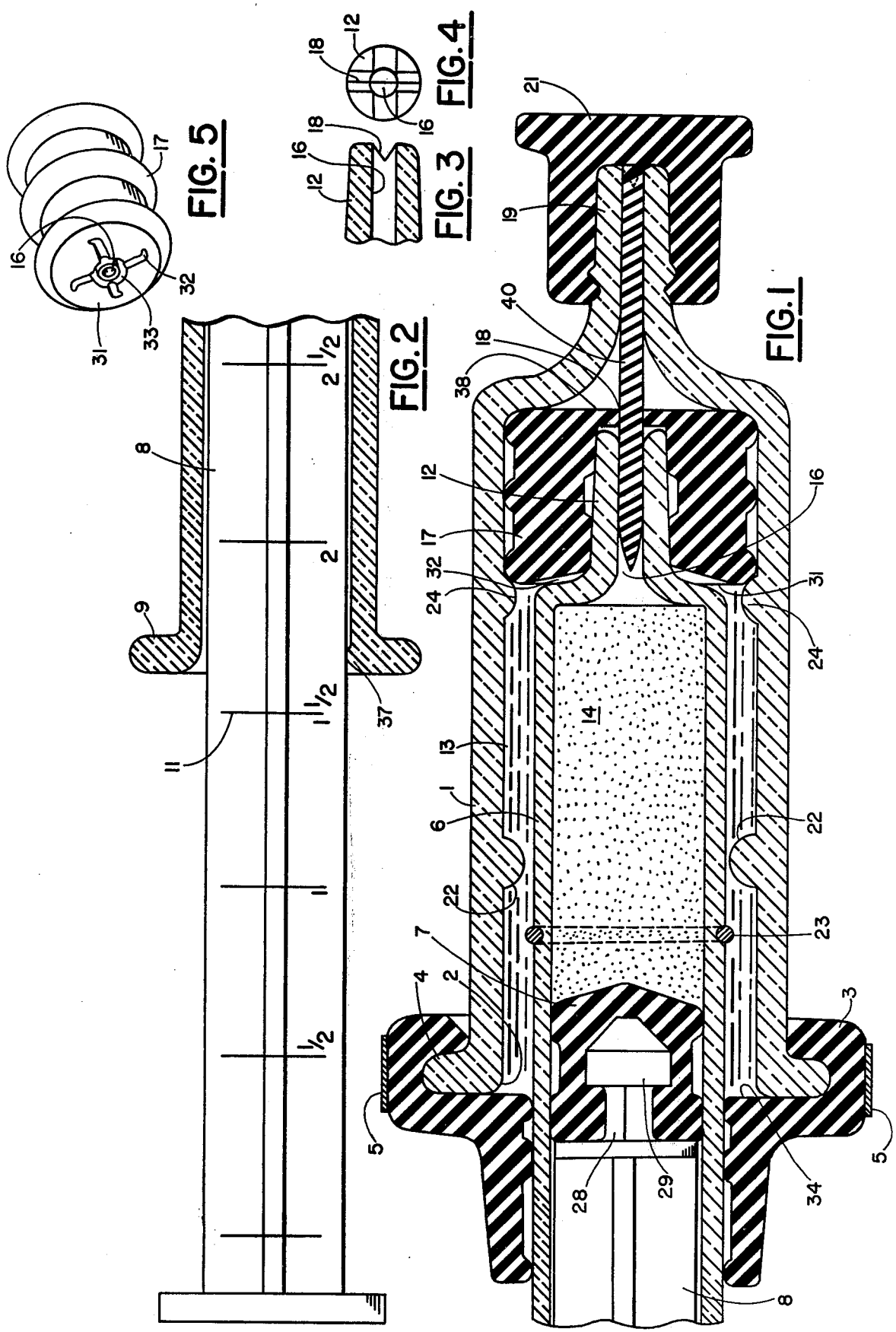

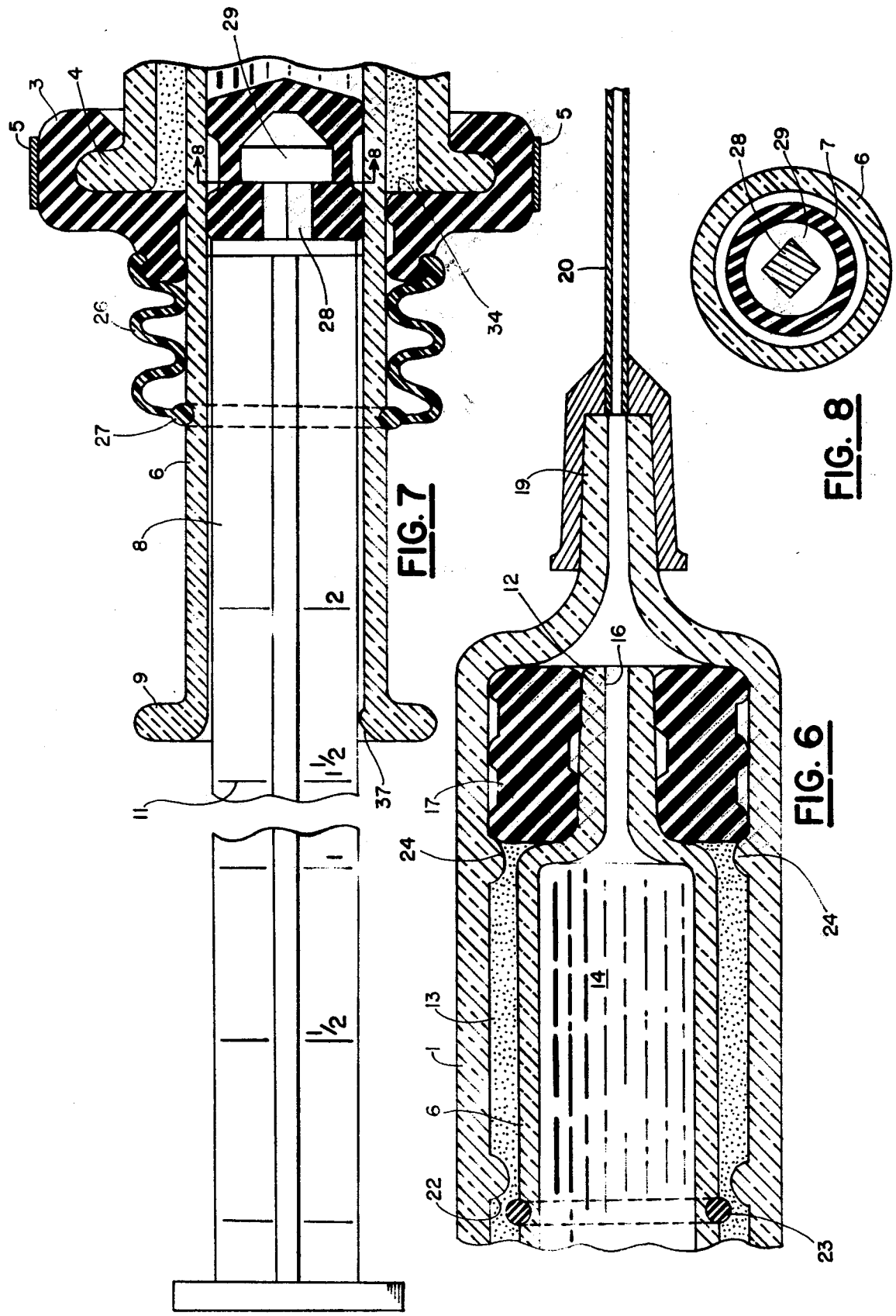

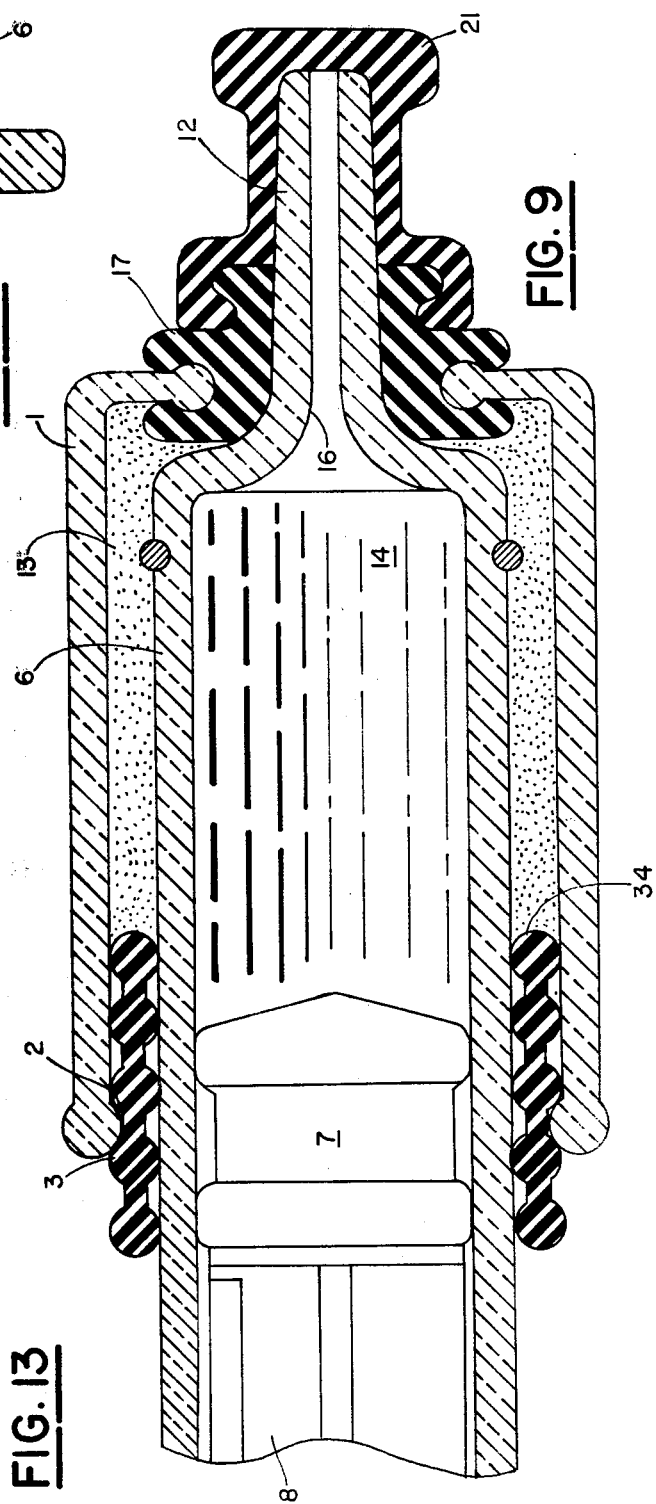
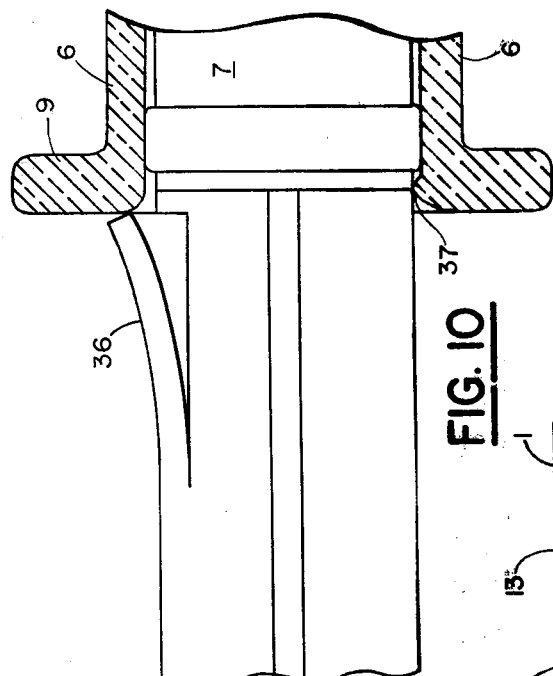
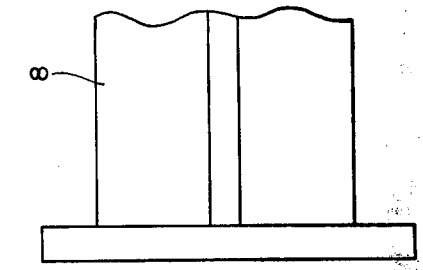
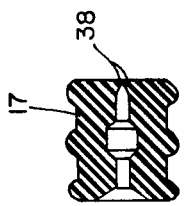
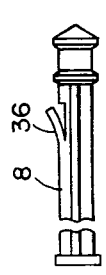

COMPARTMENTAL SYRINGE

BACKGROUND OF THE INVENTION

Various types of syringes are known at present with means for mixing components or ingredients. Some are too complex for mass production and others do not accomplish a hermetic seal of the ingredients before intermixture and do not preserve them in a sterile state. Others have to be assembled before use and others are not disposable, still others are difficult to work without error.

The primary object of the invention is to provide a syringe wherein the pressures in the outer chamber and in the inner chamber are so regulated during operation as to prevent excessive pressure in the outer chamber and facilitate discharge from the inner chamber without blockage, and allow intermixture without disassembling the device or without admitting any gas or air from the atmosphere.

Another object of the invention is to provide a device which has the ability to lyophilize in the inner chamber or in the outer chamber and which also has the ability to store medicinal ingredients under positive or negative pressure environment; and wherein agitation or mixing of diluent and powder ingredients can be rapidly and efficiently accomplished.

Another object of the invention is to provide a combination syringe and mixer wherein the operative sealed portion of the cylinder surface is protected against contamination while manipulated for mixing and then manipulated for positioning for injection.

Another object of the invention is to provide a combined syringe and mixer capable of separately containing the ingredients to be mixed, and which is positively manipulatable for intermixing by the operation of a plunger; and which imparts a swirling pulsating action to the ingredients expelled from an inner chamber for thorough mixing with the contents of an outer chamber, and in which the parts in contact with the ingredients and with the mixture are maintained in sterile condition.

Another object of the invention is to provide a combined syringe and mixer which can be used easily without inservice training, and which can be manufactured at low cost, and which is capable of accurate release of ingredients, and the principals of which can be incorporated into syringes of any size.

Other advantages and features of the invention will be evident from the disclosure herein.

BRIEF DESCRIPTION OF THE DRAWINGS

FIG. 1 is a longitudinal sectional view of the portion of the device containing the ingredients.

FIG. 2 is a fragmental view showing the manipulating portion of the cylinder and the stem of the plunger.

FIG. 3 is a fragmental view showing the discharge end of the nozzle on the cylinder and its mixing grooves therein.

FIG. 4 is a face view of the discharge end of the nozzle showing the grooves in the end.

FIG. 5 is a perspective view of the gland for the cylinder nozzle showing the spiral radial grooves.

FIG. 6 is a longitudinal sectional view of the discharge portion of a modified form of the syringe.

FIG. 7 is a fragmental partial longitudinal sectional view of the handle portion of the modified form of the syringe.

FIG. 8 is a cross-sectional view of the plunger in the inner cylinder taken on lines 8—8 of FIG. 7.

FIG. 9 is a fragmental view of another modified form of the syringe in storage position.

FIG. 10 is a fragmental view of the modified form of the syringe of FIG. 9 at the plunger end with the plunger in outermost position.

FIG. 11 is a fragmental detailed view of the plunger.

FIG. 12 is a cross-sectional view of the nozzle gland with a split valve.

FIG. 13 is a face view of the discharge end of the nozzle gland.

DETAILED DESCRIPTION

An outer casing 1 has an open end 2 which is covered by an outer seal 3 on a flange 4, tightly pressed on by a band 5. The other end of the outer casing is adapted to accommodate a syringe needle in a manner to be hereinafter described.

A cylinder 6 extends through the outer seal 3 and a plunger 7 works in the cylinder. A stem 8 of the plunger 7 extends beyond the outer end 9 of the cylinder 6. The stem 8 has graduations 11 thereon corresponding to the volume of the cavity of the cylinder in various positions of the plunger 7. The inner end of the cylinder 6 is an elongated nozzle 12. The cylinder 6 is of smaller diameter than the inside diameter of the outer casing 1 and thereby forms an outer chamber 13. The cavity in the cylinder forms an inner chamber 14. The outer chamber 13 and the inner chamber 14 communicate through the passage 16 of the nozzle 12. The nozzle 12 is sealed by a nozzle gland 17 which, in the form shown in FIG. 1, is inside of the nozzle end of the outer chamber 13. As the cylinder 6 is pulled outwardly so as to withdraw the nozzle 12 from the gland 17, the capacity of the outer chamber is enlarged because the outer diameter of the nozzle is smaller than the cylinder diameter. The tip of the nozzle 12 has cross grooves 18 in its face which facilitate picking up and sucking the mixture back into the inner cylinder chamber.

Various means may be provided adjacent the discharge nozzle 12 of the cylinder 6 for communicating the discharge from said cylinder with a syringe needle. For instance in the form shown in FIG. 1 the casing 1 terminates in a casing nozzle 19 adapted to receive a syringe needle, 20 such as shown in FIG. 6. The nozzle 19 is covered by a sealing cap 21. The casing 1 has guide projections 22 on its inner periphery, to inhibit the tilting of the cylinder 6. A limit ring 23 on the outer periphery of the cylinder 6 limits the outward stroke of the cylinder 6. Projections 24 on the inner periphery of the casing 1 adjacent to gland 17 hold the compressible gland 17 in position as the nozzle 12 is withdrawn therefrom.

The form shown in FIGS. 6 and 7 is substantially the same as the form shown in FIG. 1, except that the outer seal 3 has an accordion sleeve 26 thereon. The inner end of the accordion sleeve 26 is secured to the outer seal 3 and the outer end of the accordion sleeve has a ring 27 in a groove on the cylinder 6. This hermetically insulates the working portion of the outer surface of the cylinder against contamination. FIG. 6 also shows the manner of attachment of the needle to the casing nozzle 19. FIG. 8 shows the angular neck 28 under the securing head 29 on the end of the stem 8 on which the plunger 7 is mounted so that the stem does not rotate in the plunger 7.

The embodiment of the invention shown in FIGS. 9 and 10 is substantially the same as the first form heretofore described, except that the gland 17 is on the extreme end of the outer casing 1, and the nozzle 12 of the cylinder 6 projects through the nozzle gland 17 to the outside and beyond the casing 1 and is covered by the sealing cap 21. In this form the nozzle 12 functions both as a mixer and also the nozzle to which the syringe needle is attached. In other respects this form operates the same way as the first form.

On the face 31 of the nozzle gland 17 facing the cylinder 6 are a plurality of spiral grooves 32 radiating from a central indent 33 around the passage through the nozzle gland 17. The limit of outward movement of the cylinder 6 is such that when the cylinder is pulled through the outer gland 3 the end of the tip of the cylinder nozzle 12 is spaced at a very short clearance from the adjacent face 31 of the nozzle gland 17 whereby the material expelled from the nozzle 12 is deflected through the grooves 32 and acquires a swirling action to assist in mixing the material with the contents of the outer chamber.

The exact location of the tip of the cylinder nozzle 12 is accomplished by spacing the limit ring 23 on the cylinder 6 from the inside face 34 of the outer seal 3 to a distance slightly longer than the length of the cylinder nozzle 12 inserted into the passage of the nozzle gland 17 so that as the cylinder 6 is withdrawn from the casing 1 it is stopped when the tip of the cylinder nozzle is properly located relatively to the inner face 31 and the grooves 32 of the nozzle gland 17. In this form the outer gland 3 also extends over the cylinder 6 to a distance longer than the portion of the nozzle 12 in the passage of the nozzle gland 17 to protect against contamination. A spring stop 36 is part of the stem 8 in such position that when depressed it remains concealed in the stem 8 during the mixing operation, but when the plunger is pulled out to abut an abutment 37 to suck into the cylinder all the mixture, then the spring stop 36 is freed and expands to prevent suction in the outer chamber from drawing the plunger inwardly while rejamming the cylinder 6. The spring stop 36 is depressed for insertion into the cylinder when the mixture is to be expelled through the needle.

The nozzle gland 17 shown in the forms of FIGS. 1 and 6 may be provided with a slit valve consisting of a pair of weakened resilient projections 38 at the discharge face of the nozzle 17 oppositely to form a closed slit 39, as shown in FIGS. 12 and 13, which are parted only under a predetermined pressure to open the slit 39, and thus the gland 17 is part of the means for communicating the discharge from the cylinder with the syringe needle.

The cap 21 has a plug 40 extended from the base of the hollow hub of the cap 21, which plugs the passage of the casing nozzle 19 to prevent escapement of the material from the casing during storage. The plug 40 also plugs the cylinder nozzle 12.

In operation, first the unit is assembled. An illustrative way of assembling is herein described. The cylinder 6 is in the outer casing with the nozzle 12 in the gland 17 plugged by the plug 40 and slit 39. One of the ingredients, such as liquid in FIG. 1 or powder in FIG. 6, is introduced into the outer chamber 13. Then the outer seal 3 is sprung over the casing flange 4 and over the cylinder 6. The other ingredient, such as a powder in FIG. 1 or a liquid in FIG. 6 is then introduced into the cylinder 6. Finally, the compressible plunger 7 is pushed over the abutment 37 into the cylinder 6 up to the spring stop 36 of the stem 8. During this insertion a small tube is inserted along the plunger side to vent the air from the inner chamber. The unit is thus hermetically sealed and the sterility of the interior moving parts and of the components in the chambers is preserved and accidental intermixture is positively prevented during storage.

In use, the cylinder 6 is pulled outwardly until the limit ring 23 abuts the inner face 34 of the outer seal 3, thereby locating the discharge tip of the cylinder 12 at the proper clearance relative to the grooves 32. Then the spring stop 36 is depressed into the stem 8 and plunger 7 is reciprocated repeatedly, alternately to expel the component from the inner chamber 14 into the outer chamber 13 and then to suck the mixed components back into the inner chamber 14 until the components are completely intermixed. The outer periphery of the nozzle 12 is of smaller diameter than the outside diameter of the cylinder 6. Therefore, the withdrawing of the nozzle 12 into the outer chamber 13 enlarges the capacity of the outer chamber and creates a suction effect which assists in expelling the contents from the inner chamber by the plunger 7. All the mixture is then sucked into the inner chamber 14 as the plunger 7 is pulled back to the abutment 37 and the spring stop 36 expands into blocking position to hold the plunger in position and prevent the suction in the empty outer chamber from drawing the plunger and the mixture inwardly while the nozzle 12 is jammed into the passage of the nozzle gland 17 by pushing cylinder 6 inwardly.

Finally, the cap 21 is removed and the needle or other useful tip is placed on the casing nozzle 19, the spring stop 36 is depressed, the plunger 7 is pushed to expel the mixture through the needle with comparatively great force, depending on the rate of advance of the plunger per second and on the diameter of the tip of the nozzle 12. In the form shown in FIG. 9 the needle is placed on the cylinder nozzle 12, otherwise the operation is substantially as heretofore described.

I claim:

1. A compartmental syringe comprising
   an outer casing,
   a cylinder within the outer casing being spaced from the inner periphery of the outer casing forming an outer chamber, the interior of said cylinder forming an inner chamber, said cylinder being axially reciprocable in said outer housing,
   sealing means at one end of the outer casing, said cylinder extending through said sealing means,
   a plunger working in the cylinder,
   a discharge nozzle on the inner end of the cylinder within said outer casing,
   nozzle sealing means normally to seal said discharge nozzle from the outer chamber in an initial position,
   said nozzle sealing means unsealing said nozzle when withdrawn from said nozzle sealing means so as to communicate said inner chamber and outer chamber, whereby the working of the plunger intermixes the contents of the inner and outer chambers and sucks the mixture into the inner chamber, and whereby said nozzle sealing means reseals said nozzle upon the reinsertion of said inner cylinder to said initial position.

2. The syringe specified in claim 1 and
   openable obstruction means adjacent the discharge nozzle of said cylinder for communicating the discharge from said cylinder with a syringe needle.

3. The syringe specified in claim 2 and said means for communicating including a nozzle projection on the outer casing adapted to receive an applicator.

4. The syringe specified in claim 1, and
said discharge nozzle being projectible through said nozzle sealing means, and being adapted to receive an applicator.

5. The syringe as specified in claim 1, and
coacting means on said cylinder and on said outer casing to limit the stroke of said cylinder away from said sealing means thereby to locate the tip of said discharge nozzle at a predetermined clearance from said nozzle sealing means.

6. The syringe specified in claim 1, and
the capacity of said outer chamber and of said inner chamber being substantially equal, and the outer diameter of said discharge nozzle being smaller than the outer diameter of the cylinder whereby the withdrawal of the cylinder from the nozzle sealing means creates a suction effect facilitating intermixture by the working of said plunger.

7. The syringe specified in claims 1 or 5, or 6 and
said nozzle sealing means having a side facing said cylinder
deflecting means on said face imparting whirling effect to the material discharge from said discharge nozzle for intermixture with the material in the outer chamber.

8. The syringe specified in claims 1 or 5, and
said nozzle sealing means having a passage therethrough receiving said discharge nozzle, and having a face facing said discharge nozzle,
deflecting means on said face adjacent said passage for deflecting flow issuing from said discharge nozzle generally laterally thereby to enhance the intermixing of the contents of said chambers.

9. The syringe specified in claims 1 or 5, and
said nozzle sealing means being a gland having a passage therethrough fitting said discharge nozzle, and a releasable obstruction in said passage inhibiting discharge through said passage until the force of said discharge exceeds a predetermined pressure.

10. The syringe specified in claims 1, or 2, or 3, or 4, or 5, or 6, and
means on said casing engaging said nozzle sealing means so as to resist movement of said nozzle sealing means with the nozzle during the withdrawal of the nozzle from said nozzle sealing means.

11. The syringe specified in claims 1, or 2, or 3, or 4, or 5, or 6, and
guiding means in said outer casing inhibiting tilting of said cylinder in said casing.

12. The syringe specified in claims 1, or 2, or 3, or 4, or 5, or 6, and
manipulating means connected to said plunger, including releasable stop means to prevent inward movement of said plunger from its outward position in response to suction from said outer chamber.

13. The syringe specified in claims 1, or 2, or 3, or 4, or 5, or 6, and
a manipulating stem extending from said plunger,
a stop resiliently retracted into said cylinder during manipulation and projecting into blocking position relatively to said cylinder in the outermost position of said plunger, thereby to prevent inward drawing of said plunger from its outermost position by suction in said chambers during reinserting said discharge nozzle into said nozzle sealing means.

14. The syringe specified in claims 1, or 2, or 3, or 5, or 6, and
a casing nozzle on said casing
a cap on the casing nozzle,
and a plug extending from said cap into said casing nozzle and into said discharge nozzle obstructing accidental discharge therefrom.

15. The syringe specified in claims 1, or 2, or 3, or 5, or 6, and
a casing nozzle on said casing,
a cap on the casing nozzle
and a plug extending from said cap into said casing nozzle and into said discharge nozzle obstructing accidental discharge therefrom,
said plug being removable with removal of said cap.

16. The syringe specified in claim 1, or 2, or 3, or 4, or 5, or 6,
and said sealing means on said casing being removable from said casing.

17. The syringe specified in each of claims 1, or 2, or 3, or 4, or 5, or 6 and an outward extension of said sealing means at said one end of the outer casing extending over said cylinder and beyond said one end of said casing for covering said cylinder to a distance in excess of the outward stroke of movement of said cylinder for the withdrawal of said discharge nozzle from said nozzle sealing means.

18. The syringe specified in each of claims 1, or 2, or 3, or 4, or 5, or 6, and
means in said cylinder to limit the outward movement of said plunger.

* * * * *